(12) United States Patent
Hercouet et al.

(10) Patent No.: US 9,877,902 B2
(45) Date of Patent: *Jan. 30, 2018

(54) OIL-RICH AQUEOUS COMPOSITION AND ITS USE IN AN OXIDATIVE COLOURING OR BLEACHING METHOD

(71) Applicant: L'Oreal, Paris (FR)

(72) Inventors: Leïla Hercouet, Neuilly Plaisance (FR); Marie Giafferi, Villemomble (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/363,759

(22) PCT Filed: Dec. 5, 2012

(86) PCT No.: PCT/EP2012/074528
§ 371 (c)(1),
(2) Date: Jun. 6, 2014

(87) PCT Pub. No.: WO2013/083642
PCT Pub. Date: Jun. 13, 2013

(65) Prior Publication Data
US 2014/0377199 A1    Dec. 25, 2014

Related U.S. Application Data

(60) Provisional application No. 61/581,160, filed on Dec. 29, 2011.

(30) Foreign Application Priority Data

Dec. 6, 2011  (FR) ..................... 11 61219

(51) Int. Cl.
| | |
|---|---|
| *A61Q 5/10* | (2006.01) |
| *A61K 8/22* | (2006.01) |
| *A61K 8/31* | (2006.01) |
| *A61K 8/39* | (2006.01) |
| *A61K 8/60* | (2006.01) |
| *A61Q 5/08* | (2006.01) |
| *A45D 19/00* | (2006.01) |
| *A45D 19/02* | (2006.01) |
| *A61K 8/34* | (2006.01) |
| *A61K 8/58* | (2006.01) |

(52) U.S. Cl.
CPC ............ *A61K 8/22* (2013.01); *A45D 19/0008* (2013.01); *A45D 19/02* (2013.01); *A61K 8/31* (2013.01); *A61K 8/34* (2013.01); *A61K 8/39* (2013.01); *A61K 8/585* (2013.01); *A61K 8/604* (2013.01); *A61Q 5/08* (2013.01); *A61Q 5/10* (2013.01); *A45D 2019/0066* (2013.01)

(58) Field of Classification Search
CPC ... A61Q 5/10; A61Q 5/08; A61K 8/22; A61K 8/345; A61K 8/604; A61K 2800/88; A61K 2800/4323
USPC ...................... 8/405; 424/62, 70.31; 132/221
See application file for complete search history.

(56) References Cited

U.S. PATENT DOCUMENTS

| | | |
|---|---|---|
| 5,716,418 A | 2/1998 | Matzik |
| 7,927,383 B2 | 4/2011 | Hercouet |
| 7,931,698 B2 | 4/2011 | Simonet |
| 2003/0150069 A1 | 8/2003 | Kleen |
| 2006/0070191 A1* | 4/2006 | Lang et al. ........................ 8/406 |
| 2010/0158844 A1* | 6/2010 | Braida-Valerio et al. .... 424/70.1 |
| 2010/0162493 A1* | 7/2010 | Audousset ............... A61K 8/31 8/416 |
| 2014/0068876 A1 | 3/2014 | Rapold |

FOREIGN PATENT DOCUMENTS

| | | |
|---|---|---|
| EP | 2 198 846 A1 | 6/2010 |
| EP | 2 198 923 A2 | 6/2010 |
| EP | 2 198 927 A2 | 6/2010 |
| FR | 2 915 886 A1 | 11/2008 |
| WO | 00/53156 A1 | 9/2000 |

OTHER PUBLICATIONS

STIC Search Report dated Dec. 17, 2014.*
International Search Report and Written Opinion dated Jan. 17, 2013, issued in International Application No. PCT/EP2012/074528, filed Dec. 5, 2012, 8 pages.

* cited by examiner

*Primary Examiner* — Elisa Elhilo
(74) *Attorney, Agent, or Firm* — Christensen O'Connor Johnson Kindness PLLC

(57) ABSTRACT

The present invention therefore relates in particular to an aqueous cosmetic composition comprising one or more fatty substances in a content ranging from 40% to 80% by weight, relative to the total weight of the cosmetic composition, one or more oxyethylenated fatty alcohols having a number of oxyethylenes less than or equal to 10, one or more alkyl-polyglucoside-type surfactants; the present invention also relates to using the cosmetic composition in an oxidative coloring or bleaching method for keratin fibers, particularly human keratin fibers such as hair.

19 Claims, No Drawings

OIL-RICH AQUEOUS COMPOSITION AND ITS USE IN AN OXIDATIVE COLOURING OR BLEACHING METHOD

The present invention relates to an aqueous cosmetic composition comprising one or more fatty substances, one or more oxyethylenated fatty alcohols having a number of oxyethylenes less than or equal to 10 and one or more alkylpolyglucoside-type surfactants.

The present invention relates to the fields of the dyeing or bleaching of keratin fibres and more particularly to the fields of hair dyeing or bleaching.

It is known practice to obtain "permanent" colourations with dyeing compositions containing oxidative dye precursors, which are generally known as oxidation bases, such as ortho- or para-phenylenediamines, ortho- or para-aminophenols and heterocyclic compounds. These oxidation bases are colourless or weakly coloured compounds that, in combination with oxidizing products, can give rise to coloured compounds by an oxidative condensation method.

It is also known that the shades obtained with these oxidation bases may be varied by combining them with couplers or colouration modifiers, the latter being chosen especially from aromatic meta-diamines, meta-aminophenols, meta-diphenols and certain heterocyclic compounds such as indole compounds. The variety of the molecules used as oxidation bases and couplers allows a rich palette of colours to be obtained.

This oxidative dyeing method therefore consists in applying, to the keratin fibres, bases or a mixture of bases and couplers with hydrogen peroxide ($H_2O_2$ or aqueous hydrogen peroxide solution), as oxidizing agent, in leaving to diffuse, and in then rinsing the fibres.

The resulting colours must meet a certain number of requirements, particularly these colours must be strong and resistant to external agents, in particular to light, bad weather, washing operations, perspiration and rubbing actions. Moreover, the dyes must also make it possible to cover white hairs satisfactorily, and to be extremely unselective, i.e. to produce the smallest possible differences in colour along a single keratin fibre, which can indeed have a sensitivity effect (i.e. damage) that differs between its tip and its root.

There is a constant need to improve the colorimetric properties of hair colouring compositions, in particular as regards colour intensity delivered by oxidative dyes.

Moreover, it is also known to lighten keratin fibres with oxidizing compositions generally containing hydrogen peroxide, optionally combined with peroxygenated salts such as persulfates.

There is also a constant need to improve the properties of hair colouring compositions, in particular as regards the intensity or speed of bleaching by the oxidizing agents, particularly to reduce the risks of hair degradation.

For a few years, hair colouring/bleaching compositions that are rich in fatty substances have been developed. Such compositions are for example described in patent application FR 2940083. These compositions that may reduce hair degradation are not always satisfactory in terms of dyeing properties.

Accordingly, the present invention relates to an aqueous cosmetic composition comprising:
(i) one or more fatty substances in a content ranging from 40% to 80% by weight, relative to the total weight of the cosmetic composition.
(ii) one or more oxyethylenated fatty alcohols having a number of oxyethylenes less than or equal to 10, and
(iii) one or more alkylpolyglucoside-type surfactants.

The cosmetic composition in accordance with the present invention improves the efficacy of oxidative colouring and bleaching methods for keratin fibres.

More specifically, the cosmetic composition according to the invention improves the efficacy of oxidative dyes on keratin fibres when it is used during an oxidation colouring method, which leads to more intense colours.

Moreover, oxidative colouring methods using the cosmetic composition according to the invention may also lead to chromatic and/or sparingly selective colours, i.e. colours that are homogeneous all along the fibre.

More specifically, the cosmetic composition according to the invention improves the lightening of keratin fibres when it is used during a bleaching method with or without oxidative dyes.

The present invention also relates to a method for bleaching keratin fibres, particularly human keratin fibres such as hair, comprising the application to said fibres of a cosmetic composition as defined hereinbefore in the presence of one or more chemical oxidizing agents and optionally one or more alkaline agents, for long enough to deliver the desired lightening effect.

The present invention also relates to a method for colouring keratin fibres, particularly human keratin fibres such as hair, comprising the application to said fibres of a cosmetic composition as defined hereinbefore and one or more oxidative dyes, and optionally one or more alkaline agents, in the presence of one or more oxidizing agents, for long enough to develop the desired colour.

According to a first variant, the method for colouring keratin fibres, particularly human keratin fibres such as hair, uses a cosmetic composition (A) as defined hereinbefore, a dyeing composition (B) comprising one or more oxidative dyes and optionally one or more alkaline agents, and an oxidizing composition (C) comprising one or more chemical oxidizing agents.

A second variant of this method for colouring keratin fibres, particularly hair, uses a cosmetic composition (A) as defined hereinbefore and comprising one or more oxidative dyes and optionally one or more alkaline agents, and an oxidizing composition (C) comprising one or more chemical oxidizing agents.

The invention also relates to using an aqueous cosmetic composition as defined hereinbefore comprising one or more oxidative dyes to improve the colour intensity of the keratin fibres, particularly human keratin fibres such as hair.

The invention also relates to using an aqueous cosmetic composition as defined hereinbefore comprising one or more oxidizing agents to improve the lightening of the keratin fibres, particularly human keratin fibres such as hair.

Lastly, the present invention relates to a multi-compartment device using a first compartment containing the aqueous cosmetic composition as defined hereinbefore, a second compartment containing a cosmetic composition comprising one or more oxidative dyes, and a third compartment containing one or more chemical oxidizing agents, one or more alkaline agents being preferably present in the first and/or second compartment.

Chemical oxidizing agent means an oxidizing agent other than air.

It also relates to a multi-compartment device using a first compartment containing the aqueous cosmetic composition as defined hereinbefore, and optionally one or more oxidative dyes, and a second compartment containing one or more chemical oxidizing agents, one or more alkaline agents being preferably present in the first compartment.

Other features, aspects, subjects and benefits of the present invention will emerge even more clearly on reading the description and the examples that follow.

Fatty substance means an organic compound that is insoluble in water at ordinary temperature (25° C.) and at atmospheric pressure (760 mmHg), i.e. solubility of less than 5%, preferably 1% and even more preferentially 0.1%. They present in their structure at least one chain of at least two siloxane groups or a hydrocarbon-based chain containing at least 6 carbon atoms. In addition, the fatty substances are generally soluble in organic solvents under the same temperature and pressure conditions, for instance chloroform, ethanol, benzene, liquid petrolatum or decamethylcyclopentasiloxane.

According to a specific embodiment, the fatty substance is other than a fatty acid.

The fatty substances are in particular chosen from $C_6$-$C_{16}$ lower alkanes, non-silicone oils of animal, plant, mineral or synthetic origin, non-oxyalkylenated fatty alcohols, fatty acid and/or fatty alcohol esters, non-silicone waxes and silicones.

For the purposes of the invention, the fatty alcohols and esters more particularly contain one or more linear or branched, saturated or unsaturated hydrocarbon-based groups containing 6 to 30 carbon atoms, optionally substituted, in particular with one or more hydroxyl groups (in particular 1 to 4). If they are unsaturated, these compounds may comprise from one to three conjugated or non-conjugated carbon-carbon double bonds.

As regards the $C_6$-$C_{16}$ lower alkanes, they are linear or branched, or optionally cyclic. By way of example, the alkanes may be chosen from hexane, undecane, dodecane and tridecane, isoparaffins such as isohexadecane and isodecane.

As non-silicone oils of animal, plant, mineral or synthetic origin that may be used in the composition of the invention, examples that may be mentioned include:

hydrocarbon oils of animal or plant origin, such as perhydrosqualene;

triglyceride oils of vegetable or synthetic origin, such as liquid triglycerides of fatty acids containing from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarinerie Dubois or those sold under the names Miglyol® 810, 812 and 818 by the company Dynamit Nobel, jojoba oil and shea butter oil;

linear or branched hydrocarbons having more than 16 carbon atoms, of mineral or synthetic origin, such as volatile or non-volatile liquid paraffins, and their derivatives, petrolatum, liquid petrolatum, polydecenes, and hydrogenated polyisobutene such as Parleam®;

fluoro oils, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-(trifluoromethyl)perfluoromorpholine sold under the name PF 5052® by the company 3M.

The non-oxyalkylenated fatty alcohols that may be used in the aqueous cosmetic composition are saturated or unsaturated, linear or branched and contain from 6 to 30 carbon atoms and more particularly from 8 to 30 carbon atoms; mention may be made of cetyl alcohol, stearyl alcohol and their mixture (cetylstearyl alcohol), octyldodecanol, 2-butyloctanol, 2-hexyldecanol, 2-undecylpentadecanol, oleyl alcohol or linoleyl alcohol.

The fatty acids that may be used in the aqueous cosmetic composition may be chosen from saturated or unsaturated carboxylic acids containing from 6 to 30 carbon atoms and in particular from 9 to 30 carbon atoms. They are more specifically chosen from myristic acid, palmitic acid, stearic acid, behenic acid, oleic acid, linoleic acid, linolenic acid and isostearic acid.

The esters of a fatty acid and/or of a fatty alcohol, which are advantageously different than the triglycerides mentioned above are esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this alternative form, use may also be made of esters of $C_4$-$C_{22}$ di- or tricarboxylic acids and of $C_1$-$C_{22}$ alcohols and esters of mono-, di- or tricarboxylic acids and of di-, tri-, tetra- or pentahydroxy $C_2$-$C_{26}$ alcohols.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate.

The composition can also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and that comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose, lactose and their derivatives, in particular alkyl derivatives, such as methyl derivatives, for example methylglucose.

The esters of sugars and of fatty acids can be chosen in particular from the group consisting of the esters or mixtures of esters of sugars described above and of saturated or unsaturated and linear or branched $C_6$-$C_{30}$ and preferably $C_{12}$-$C_{22}$ fatty acids. If they are unsaturated, these compounds may comprise from one to three conjugated or non-conjugated carbon-carbon double bonds.

The esters according to this alternative form can also be chosen from mono-, di-, tri- and tetraesters, polyesters and their mixtures.

These esters can, for example, be oleates, laurates, palmitates, myristates, behenates, cocoates, stearates, linoleates, linolenates, caprates, arachidonates or their mixtures, such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose.

Mention may be made, by way of example, of the product sold under the name Glucate® DO by Amerchol, which is a methylglucose dioleate.

Mention may also be made, by way of examples of esters or mixtures of esters of sugar and of fatty acid, of:
the products sold under the names F160, F140, F110, F90, F70 and SL40 by Crodesta, respectively denoting sucrose palmitate/stearates formed of 73% monoester and 27% di- and triester, of 61% monoester and 39% di-, tri- and tetraester, of 52% monoester and 48% di-, tri- and tetraester, of 45% monoester and 55% di-, tri- and tetraester, and of 39% monoester and 61% di-, tri- and tetraester, and sucrose monolaurate;
the products sold under the name Ryoto Sugar Esters, for example referenced B370 and corresponding to sucrose behenate formed of 20% monoester and 80% diester, triester and polyester;
the sucrose monopalmitate/stearate-dipalmitate/stearate sold by Goldschmidt under the name Tegosoft® PSE.

The non-silicone wax(es) that may be used in the aqueous cosmetic composition (A) are chosen in particular from carnauba wax, candelilla wax, esparto grass wax, paraffin wax, ozokerites, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the invention are especially marine waxes such as the product sold by the company Sophim under the reference M82, and polyethylene waxes or polyolefin waxes in general.

The silicones that can be used in the aqueous cosmetic composition of the present invention are volatile or non-volatile and cyclic, linear or branched silicones, which are unmodified or modified by organic groups, having a viscosity from $5 \times 10^{-6}$ to 2.5 m²/s at 25° C. and preferably from $1 \times 10^{-5}$ to 1 m²/s.

The silicones that can be used in accordance with the invention can be provided in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in more detail in Walter Noll's "Chemistry and Technology of Silicones" (1968), Academic Press. They can be volatile or non-volatile.

When they are volatile, the silicones are more particularly chosen from those having a boiling point of between 60° C. and 260° C., and more particularly still from:

(i) cyclic polydialkylsiloxanes comprising from 3 to 7 and preferably from 4 to 5 silicon atoms. They are, for example, octamethylcyclotetrasiloxane, sold in particular under the name Volatile Silicone® 7207 by Union Carbide or Silbione® 70045 V2 by Rhodia, decamethylcyclopentasiloxane, sold under the name Volatile Silicone® 7158 by Union Carbide and Silbione® 70045 V5 by Rhodia, and their mixtures.

Mention may also be made of cyclocopolymers of the dimethylsiloxane/methylalkylsiloxane type, such as Volatile Silicone® FZ 3109, sold by Union Carbide, having the formula:

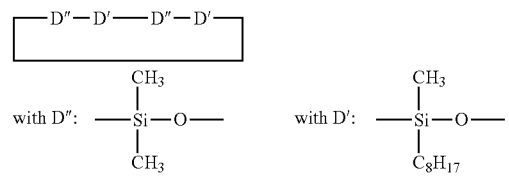

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-1,1'-bis(2,2,2', 2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m²/s at 25° C. An example is decamethyltetrasiloxane sold in particular under the name SH 200 by the company Toray Silicone. Silicones coming within this category are also described in the paper published in Cosmetics and Toiletries, Vol. 91, January 76, pp. 27-32, Todd & Byers, "Volatile Silicone Fluids for Cosmetics".

Use is preferably made of non-volatile polydialkylsiloxanes, of polydialkylsiloxane gums and resins, of polyorganosiloxanes modified by the above organic functional groups, and of their mixtures.

These silicones are more particularly chosen from polydialkylsiloxanes, among which mention may be made mainly of polydimethylsiloxanes having trimethylsilyl end groups. The viscosity of the silicones is measured at 25° C. according to Standard ASTM 445 Appendix C.

Mention may be made, among these polydialkylsiloxanes, without implied limitation, of the following commercial products:

the Silbione® oils of the 47 and 70 047 series or the Mirasil® oils sold by Rhodia, such as, for example, the oil 70 047 V 500 000;

the oils of the Mirasil® series sold by Rhodia;

the oils of the 200 series from Dow Corning, such as DC200 having a viscosity of 60 000 mm$^2$/s;

the Viscasil® oils from General Electric and certain oils of the SF series (SF 96, SF 18) from General Electric.

Mention may also be made of polydimethylsiloxanes having dimethylsilanol end groups known under the name of dimethiconol (CTFA), such as the oils of the 48 series from Rhodia.

Mention may also be made, in this category of polydialkylsiloxanes, of the products sold under the names Abil Wax® 9800 and 9801 by Goldschmidt, which are polydi ($C_1$-$C_{20}$)alkylsiloxanes.

The silicone gums that can be used in accordance with the invention are in particular polydialkylsiloxanes and preferably polydimethylsiloxanes having high number-average molecular weights of between 200,000 and 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or their mixtures.

Products that can be used more particularly in accordance with the invention are mixtures, such as:

the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by Dow Corning;

the mixtures of a polydimethylsiloxane gum and of a cyclic silicone, such as the product SF 1214 Silicone Fluid from General Electric; this product is an SF 30 μm corresponding to a dimethicone, having a number-average molecular weight of 500 000, dissolved in the oil SF 1202 Silicone Fluid corresponding to decamethylcyclopentasiloxane;

the mixtures of two PDMSs with different viscosities, and more particularly of a PDMS gum and a PDMS oil, such as the product SF 1236 from General Electric. The product SF 1236 is the mixture of a gum SE 30 defined above having a viscosity of 20 m$^2$/s and of an oil SF 96 with a viscosity of $5 \times 10^{-6}$ m$^2$/s. This product preferably comprises 15% of gum SE 30 and 85% of an oil SF 96.

The organopolysiloxane resins that can be used in accordance with the invention are cross-linked siloxane systems including the following units:

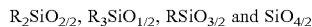

$R_2SiO_{2/2}$, $R_3SiO_{1/2}$, $RSiO_{3/2}$ and $SiO_{4/2}$ in which R denotes an alkyl having from 1 to 16 carbon atoms. Among these products, those that are particularly preferred are those in which R denotes a lower $C_1$-$C_4$ alkyl group, more particularly methyl.

Mention may be made, among these resins, of the product sold under the name Dow Corning 593 or those sold under the names Silicone Fluid SS 4230 and SS 4267 by General Electric, which are silicones of dimethyl/trimethylsiloxane structure.

Mention may also be made of the resins of the trimethylsiloxysilicate type, sold in particular under the names X22-4914, X21-5034 and X21-5037 by Shin-Etsu.

The organomodified silicones that can be used in accordance with the invention are silicones as defined above and comprising, in their structure, one or more organic functional groups attached via a hydrocarbon group.

In addition to the silicones described above, the organo-modified silicones can be polydiarylsiloxanes, in particular polydiphenylsiloxanes, and polyalkylarylsiloxanes functionalized by the abovementioned organic functional groups.

The polyalkylarylsiloxanes are chosen in particular from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

some of the oils in the SF series from General Electric, such as SF 1023, SF 1154, SF 1250 and SF 1265.

Mention may be made, among the organomodified silicones, of polyorganosiloxanes comprising:

polyethyleneoxy and/or polypropyleneoxy groups optionally comprising $C_6$-$C_{24}$ alkyl groups, such as the products named dimethicone copolyol sold by Dow Corning under the name DC 1248 or the oils Silwet® L 722, L 7500, L 77 and L 711 by Union Carbide, and the ($C_{12}$)alkyl methicone copolyol sold by Dow Corning under the name Q2 5200;

substituted or unsubstituted amino groups, such as the products sold under the names GP 4 Silicone Fluid and GP 7100 by Genesee or the products sold under the names Q2 8220 and Dow Corning 929 or 939 by Dow Corning. The substituted amino groups are in particular $C_1$-$C_4$ aminoalkyl groups;

alkoxylated groups, such as the product sold under the name Silicone Copolymer F-755 by SWS Silicones, and Abil Wax® 2428, 2434 and 2440 by Goldschmidt.

The fatty substances do not comprise any $C_2$-$C_3$ oxyalkylene units.

More particularly, the fatty substances are chosen from compounds that are liquid or pasty at room temperature and atmospheric pressure.

Preferably, the fatty substance is a compound that is liquid at the temperature of 25° C. and at atmospheric pressure.

Preferably, the fatty substance(s) of the composition according to the invention are non-silicone.

The fatty substances are preferably chosen from $C_6$-$C_{16}$ lower alkanes, non-oxyalkylenated fatty alcohols, fatty acid and/or fatty alcohol esters, non-silicone oils of mineral, plant or synthetic origin, including in particular linear or branched hydrocarbons with more than 16 carbon atoms.

According to one embodiment, the fatty substance(s) are chosen from liquid petrolatum, 2-octyldodecanol, perhydrosqualene, polydecenes, and liquid esters of fatty acids and/or of fatty alcohols, or their mixtures.

Specifically, the fatty substance preferably present in the cosmetic composition is liquid petrolatum, octyl-2-dodecanol and perhydrosqualene.

According to a preferred embodiment, the fatty substance present in the cosmetic composition is liquid petrolatum.

The aqueous cosmetic composition according to the invention comprises from 40 to 80% by weight of fatty substance, and in particular from 40% to 60% by weight, relative to the total weight of the composition.

The cosmetic composition according to the present invention further comprises one or more oxyethylenated fatty alcohols having a number of oxyethylenes less than 10.

For the purposes of the present invention, oxyethylenated fatty alcohol means any oxyethylenated alcohol having a hydrocarbon chain containing at least 6 carbon atoms.

According to the invention, oxyethylenated fatty alcohol means any fatty alcohol having the following structure:

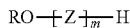

in which:

R denotes a saturated or unsaturated, linear or branched radical containing from 6 to 40 carbon atoms, particularly from 8 to 30, preferably below 16, more preferably from 10 to 15 and Z denotes an oxyethylenated radical having the following formula (I):

$$—CH_2—CH_2—O— \qquad (I)$$

m denotes the number of ethylene oxide groups below 10, preferably ranging from 2 to 10.

Particularly preferred liquid oxyethylenated fatty alcohols according to the invention are saturated or unsaturated, linear fatty alcohols, containing from 10 to 20 carbon atoms, in particular 12 carbon atoms, and from 2 to 8 ethylene oxide groups, particularly two ethylene oxide groups.

Mention may be in particular made of the following commercially available products as oxyalkylenated fatty alcohol-type compounds:

Mergital LM2 (Cognis) [lauryl alcohol 2 EO];

Empilan KA 2.5/90FL (Albright & Wilson) and Mergital BL309 (Cognis) [decyl alcohol 3 EO];

Empilan KA 5/90FL (Albright & Wilson) and Mergital BL589 (Cognis) [decyl alcohol 5 EO];

Emulgin 05 (Cognis) [oleocetyl alcohol 5 EO].

Preferably, the oxyethylenated fatty alcohol present in the cosmetic composition according to the invention is lauryl alcohol comprising two ethylene oxide groups.

The oxyethylenated fatty alcohol(s) having a number of ethylene oxides below 10 may be present in the cosmetic composition according to the invention in a content ranging from 0.5 to 30% by weight, preferably in a content ranging from 1 to 15% by weight, relative to the total weight of the composition.

The cosmetic composition according to the present invention further comprises one or more alkylpolyglucoside-type surfactants.

The alkylpolyglucoside-type surfactants present in the cosmetic composition according to the present invention are more specifically represented by the following general formula (II):

in which $R_1$ designates a linear or branched alkyl and/or alkenyl radical comprising from about 8 to 24 carbon atoms, an alkylphenyl radical in which the linear or branched alkyl group comprises from about 8 to 24 carbon atoms, $R_2$ denotes an alkylene radical comprising from 2 to 4 carbon atoms, L designates a reducing sugar containing from 5 to 6 carbon atoms, a designates a value ranging from 0 to 10, and b designates a value ranging from 1 to 15.

Preferred alkylpolyglucosides according to the present invention are compounds having formula (II) in which $R_1$ designates more specifically a linear or branched alkyl and/or alkenyl radical containing from 9 to 14 carbon atoms, a designates a value ranging from 0 to 3 and even more specifically equal to zero, L designates glucose, fructose or galactose. The degree of polymerization (S) of the saccharide, i.e. the value of b in the formula (II), may range from 1 to 15. According to the invention, reducing sugars containing 80%, or more of sugars whose degree of polymerization (S) takes a value ranging from 1 to 4 are preferred.

Compounds having formula (II) are in particular represented by the products sold by Henkel as APG, such as products APG 300, APG 350, APG 500, APG 550, APG 625, APG base 10-12; products sold by Seppic as Triton CG 110 (or Oramix CG 110) and Triton CG 312 (or Oramix NS 10); those sold by B.A.S.F. as Lutensol GD 70; sold by Henkel as Plantaren 1200, Plantaren 1300, Plantaren 2000, and Plantacare 2000, Plantacare 818, Plantacare 1200.

The alkylpolyglucoside-type surfactants may be present in the cosmetic composition in a content ranging from 0.5% to 30% by weight and preferably in a content ranging from 1 to 15% by weight, relative to the total weight of the composition.

The cosmetic composition may optionally also contain one or more oxidative dyes. In this case, the cosmetic composition according to the invention corresponds to a dyeing composition for keratin fibres.

Specifically, the oxidative dyes are chosen from one or more oxidation bases, optionally combined with one or more couplers.

By way of example, the oxidation bases are chosen from para-phenylenediamines, bis(phenyl)alkylenediamines, para-aminophenols, ortho-aminophenols and heterocyclic bases, and their addition salts.

Mention may be made, among para-phenylenediamines, by way of example, of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-(β-hydroxyethylamino-5-aminotoluene, 3-hydroxy-1-(4'-aminophenyl)pyrrolidine and their addition salts with an acid.

Preference is particularly given, among the abovementioned para-phenylenediamines, to para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and their addition salts with an acid.

Mention may be made, among bis(phenyl)alkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenypethylenediamine, 1,8-bis(2,5-diaminophenoxy)-3,6-dioxaoctane and their addition salts.

Mention may be made, among para-aminophenols, by way of example, of para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, 4-amino-2-fluorophenol and their addition salts with an acid.

Mention may be made, among ortho-aminophenols, by way of example, of 2-aminophenol, 2-amino-5-methylphenol, 2-amino-6-methylphenol, 5-acetamido-2-aminophenol and their addition salts.

Mention may be made, among heterocyclic bases, by way of example, of pyridine derivatives, pyrimidine derivatives and pyrazole derivatives.

Mention may be made, among pyridine derivatives, of the compounds described, for example, in Patents GB 1 026 978 and GB 1 153 196, such as 2,5-diaminopyridine, 2-(4-methoxyphenyl)amino-3-aminopyridine, 3,4-diaminopyridine and their addition salts.

Other pyridine oxidation bases of use in the present invention are the 3-aminopyrazolo[1,5-a]pyridine oxidation bases or their addition salts described, for example, in Patent Application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl(ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and their addition salts.

Mention may be made, among pyrimidine derivatives, of the compounds described, for example, in Patents DE 2359399, JP 88-169571, JP 05-63124 and EP 0 770 375 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Mention may be made, among pyrazole derivatives, of the compounds described in Patents DE 3843892 and DE 4133957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-(hydroxymethyl)-1-methylpyrazole, 4,5-diamino-3-(hydroxymethyl)-1-isopropylpyrazole, 4,5-diamino-3-methyl-1-isopropylpyrazole, 4-amino-5-(2'-amino ethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole and their addition salts. Use may also be made of 4,5-diamino-1-(β-methoxyethyl)pyrazole.

Use will preferably be made of a 4,5-diaminopyrazole and more preferably still of 4,5-diamino-1-(β-hydroxyethyl)pyrazole and/or one of its salts.

Mention may also be made, as pyrazole derivatives, of diamino-N,N-dihydropyrazolopyrazolones and in particular those described in Application FR-A-2 886 136, such as the following compounds and their addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or one of its salts.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or one of their salts.

The cosmetic composition according to the invention may optionally comprise one or more couplers advantageously chosen from those conventionally used in the dyeing of keratin fibres.

Mention may in particular be made, among these couplers, of meta-phenylenediamines, meta-aminophenols, meta-diphenols, naphthalene couplers, heterocyclic couplers and their addition salts.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis((β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethylpyrazolo[3,2-c]-1,2,4-triazole and 6-methylpyrazolo[1,5-a]benzimidazole, their addition salts with an acid, and their mixtures.

In general, the addition salts of the oxidation bases and couplers that can be used in the context of the invention are chosen in particular from the addition salts with an acid, such as the hydrochlorides, hydrobromides, sulfates, citrates, succinates, tartrates, lactates, tosylates, benzenesulfonates, phosphates and acetates.

The oxidation base(s) each advantageously represent from 0.0001% to 10% by weight relative to the total weight of the composition, and preferably from 0.005% to 5% by weight relative to the total weight of the composition.

The content of coupler(s), if it (they) is (are) present, each advantageously represents from 0.0001% to 10% by weight, with respect to the total weight of the composition, preferably from 0.005% to 5% by weight, with respect to the total weight of the aqueous cosmetic composition.

When the composition according to the present invention contains one or more alkaline agents, the alkaline agent may be organic or inorganic or hybrid.

A first type of alkaline agents that can be used in the sense of the present invention are organic amines with a $pK_b$ at 25° C. of less than 12, preferably less than 10 and even more advantageously less than 6. It should be noted that it is the $pK_b$ corresponding to the functional group of highest basicity.

According to a first variant of the invention, the organic amine comprises a primary, secondary or tertiary amine function and one or more linear or branched $C_1$-$C_8$ alkyl groups carrying one or more hydroxyl radicals.

Organic amines chosen from alkanolamines such as monoalkanolamines, dialkanolamines or trialkanolamines, comprising one to three identical or different $C_1$-$C_4$ hydroxyalkyl radicals, are in particular suitable for implementing the invention.

Among compounds of this type, mention may be made of monoethanolamine, diethanolamine, triethanolamine, mono isopropanolamine, diisopropanolamine, N-dimethylamino ethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

Also suitable are the organic amines having the following formula:

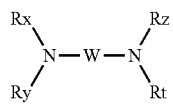

in which W is a $C_1$-$C_6$ alkylene residue optionally substituted with a hydroxyl group or a $C_1$-$C_6$ alkyl radical; Rx, Ry, Rz and Rt, which may be identical or different, denote a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

According to another variant of the invention, the organic amine is chosen from amino acids.

More particularly, the amino acids that can be used are of natural or synthetic origin, in their L, D or racemic form, and comprise at least one acid functional group chosen more particularly from carboxylic acid, sulfonic acid, phosphonic acid or phosphoric acid functional groups. The amino acids can be in the neutral or ionic form.

Advantageously, the amino acids are basic amino acids comprising an additional amine functional group optionally included in a ring or in a ureido functional group.

As amino acids that can be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

According to one preferred variant of the invention, the organic amine is chosen from basic amino acids. The amino acids that are particularly preferred are glycerine, tyrosine, arginine, lysine and histidine, and their mixtures.

According to another variant of the invention, the organic amine is chosen from organic amines of heterocyclic type. Besides histidine that has already been mentioned in the amino acids, mention may in particular be made of pyridine, piperidine, imidazole, triazole, tetrazole and benzimidazole.

According to another variant of the invention, the organic amine is chosen from amino acid dipeptides. As amino acid dipeptides that can be used in the present invention, mention may be made especially of carnosine, anserine and balenine.

According to another variant of the invention, the organic amine is chosen from compounds comprising a guanidine function. As amines of this type that may be used in the present invention, besides arginine that has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Preferably, the organic amine is an alkanolamine. More preferentially, the organic amine is chosen from 2-amino-2-methyl-1-propanol, monoethanolamine, or their mixtures. More preferentially still, the organic amine is monoethanolamine.

A second type of alkaline agents that can be used in the sense of the present invention comprises the organic or inorganic (in this case this would be hybrid alkaline agents) salts of organic amines as described hereinbefore.

Preferably, the organic salts are chosen from organic acid salts such as citrates, lactates, glycolates, gluconates, acetates, propionates, fumarates, oxalates and tartrates.

Preferably, the inorganic salts are chosen from hydrohalides (for example hydrochlorides), carbonates, hydrogen carbonates, sulfates, hydrogen phosphates and phosphates.

A third type of alkaline agents that can be used in the sense of the present invention are inorganic bases. By way of example, mention may be made of ammonia, carbonates such as sodium carbonate, potassium carbonate, ammonium carbonate, sodium hydroxide, potash, silicates and metasilicates such as sodium metasilicate, potassium metasilicate, preferably carbonates and more preferably an ammonium carbonate.

Preferably, alkaline agents that can be used in the cosmetic composition according to the invention may be chosen from organic amines and their salts, organic bases and ammonium salts. Specifically, the alkaline agent is monoethanolamine.

When the alkaline agents are present in the cosmetic composition in accordance with the present invention, these agents are present in a content ranging from 0.01 to 30% by weight, preferably from 0.1 to 20% by weight compared to the weight of said composition.

Preferably, the composition according to the invention comprises one or more alkaline agents.

The composition according to the invention preferably comprises water or a mixture of water and one or more common organic solvents.

Preferably, the composition according to the invention comprises water in a content ranging from 5% to 30% by weight, relative to the total weight of the cosmetic composition.

The composition may comprise organic solvents. Mention may more particularly be made, among suitable organic solvents, of non-aromatic alcohols, such as ethyl alcohol or isopropyl alcohol, or glycols or glycol ethers, such as, for example, ethylene glycol monomethyl, monoethyl or monobutyl ether, propylene glycol or its ethers, such as, for example, propylene glycol monomethyl ether, butylene glycol, dipropylene glycol and also diethylene glycol alkyl ethers, such as, for example, diethylene glycol monoethyl ether or monobutyl ether, or alternatively polyols, such as glycerol. Polyethylene glycols and polypropylene glycols, and mixtures of all these compounds, can also be used as solvent.

The common organic solvents described above, if they are present, usually represent from 0.1% to 15% by weight and more preferentially from 0.5% to 10% by weight relative to the total weight of the composition.

Preferably, the cosmetic composition according to the present invention comprises one or more thickening agents.

The thickening agents can be chosen from inorganic thickening agents and organic thickening agents.

The organic thickening agent(s) may be chosen from cellulose-based thickeners, for example, hydroxyethylcellulose, hydroxypropylcellulose and carboxymethylcellulose, guar gum and its derivatives, for example the hydroxypropyl guar sold by the company Rhodia under the reference Jaguar HP 105, gums of microbial origin, such as xanthan gum and scleroglucan gum, synthetic thickeners such as cross-linked acrylic acid or acrylamidopropanesulfonic acid homopolymers, for example Carbomer, non-ionic, anionic, cationic or amphoteric associative polymers, such as the polymers sold under the names Pemulen TR1 or TR2 by the company Goodrich, Salcare SC90 by the company Ciba, Aculyn 22, 28, 33, 44 or 46 by the company Rohm & Haas, and Elfacos T210 and T212 by the company Akzo.

According to one embodiment, the inorganic thickening agents are chosen from organophilic clays, fumed silicas or their mixtures.

The organophilic clay can be chosen from montmorillonite, bentonite, hectorite, attapulgite, sepiolite and their mixtures. The clay is preferably a bentonite or a hectorite.

These clays can be modified with a chemical compound chosen from quaternary ammoniums, tertiary amines, amine acetates, imidazolines, amine soaps, fatty sulfates, alkylarylsulfonates, amine oxides and their mixtures.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; quaternium-18/benzalkonium bentonites, such as those sold under the names Claytone HT and Claytone PS by Southern Clay; quaternium-18 hectorites, such as those sold under the names Bentone Gel DOA, Bentone Gel ECO5, Bentone Gel EUG, Bentone Gel IPP, Bentone Gel ISD, Bentone Gel SS71, Bentone Gel VS8 and Bentone Gel VS38 by Rheox, and Simagel M and Simagel SI 345 by Biophil.

The fumed silicas can be obtained by high-temperature pyrolysis of a volatile silicon compound in an oxyhydrogen flame, producing a finely divided silica. This method makes it possible in particular to obtain hydrophilic silicas that exhibit a large number of silanol groups at their surface. Such hydrophilic silicas are sold, for example, under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of the silica by chemical reaction for the purpose of reducing the number of silanol groups. It is possible in particular to replace silanol groups with hydrophobic groups: a hydrophobic silica is then obtained.

The hydrophobic groups can be:
trimethylsiloxyl groups, which are obtained in particular by treating fumed silica in the presence of hexamethyldisilazane. Silicas thus treated are known as "Silica silylate" according to the CTFA (6th Edition, 1995). They are sold, for example, under the references Aerosil R812® by Degussa and Cab-O-Sil TS-530® by Cabot.
dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th Edition, 1995). They are sold, for example, under the references Aerosil R972® and Aerosil R974® by the company Degussa, and Cab-O-Sil TS-610® and Cab-O-Sil TS-720® by the company Cabot.

The fumed silica preferably exhibits a particle size that can be nanometric to micrometric, for example ranging from approximately 5 to 200 nm.

Preferably, the composition comprises a hectorite, an organomodified bentonite or an optionally modified fumed silica.

The composition according to the invention may further comprise diverse conventional adjuvants well known in the state of the art such as anionic, cationic, non-ionic, amphoteric, zwitterionic polymers or their mixtures; antioxidants; penetration agents; sequestering agents; fragrances; dispersants; film-forming agents; ceramides; preservatives; opacifiers, surfactants other than alkylpolyglucosides and oxyethylenated fatty alcohols having a number of ethylene oxides less than or equal to 10.

A person skilled in the art will take care to select the optional additives and their amounts such that they do not harm the properties of the compositions of the present invention.

These additives are generally present in the composition according to the invention in an amount ranging from 0 to 20% by weight relative to the total weight of the composition.

When the composition contains water, the pH of the cosmetic composition is comprised between 2 and 12, preferably between 5 and 10.5 and particularly between 7.5 and 10.5. The pH is adapted by using acidifying or alkaline agents.

Mention may be made, among the acidifying agents, by way of example, of inorganic or organic acids, such as hydrochloric acid, orthophosphoric acid, sulfuric acid, carboxylic acids, such as acetic acid, tartaric acid, citric acid or lactic acid, or sulfonic acids.

Regarding the alkaline agent, if it is present, it may be chosen from the alkaline agents described hereinbefore.

In accordance with that stated hereinbefore, the aqueous cosmetic composition according to the present invention may also be used in a method for bleaching keratin fibres. According to this variant, the composition does not contain any oxidative dyes. In accordance with that stated hereinbefore, the aqueous cosmetic composition according to the present invention may also be used in a method for oxidatively colouring keratin fibres.

According to a first embodiment, the present invention relates to a method for dyeing keratin fibres, particularly human keratin fibres such as hair, comprising the application to said fibres of a cosmetic composition as defined hereinbefore, one or more oxidative dyes, and preferably one or more alkaline agents, in the presence of an oxidizing composition comprising one or more chemical oxidizing agents, for long enough to develop the desired colour.

According to this method, the oxidative dye(s) may be applied before or after the composition of the invention. A composition resulting from mixing these compounds can also be applied to hair.

The oxidizing composition may be added to the composition of the invention directly on the keratin fibres before or after applying the composition of the present invention. Preferably, the oxidizing composition is added to the composition of the invention at the time of use.

According to another embodiment, the present invention relates to method for dyeing keratin fibres, particularly human keratin fibres such as hair, comprising applying to said fibres:
a cosmetic composition (A) as defined previously optionally comprising one or more alkaline agents,
a dyeing composition (B) comprising one or more oxidative dyes and optionally one or more alkaline agents,
an oxidizing composition (C) comprising one or more chemical oxidizing agents.

Preferably, the dyeing composition (B) is an aqueous composition.

More preferably still, the water concentration may range from 10% to 90% by weight, better still from 20% to 80% of the total weight of the composition.

The pH of the dyeing composition (B), if it is aqueous, is between 2 and 12 and preferably between 8 and 11. The pH is adapted by using acidifying or alkaline agents such as those indicated previously.

Preferably, the dyeing composition (B) comprises one or more alkaline agents, preferably one or more organic amines, in particular alkanolamines, in particular monoethanolamine.

According to a first variant of this second embodiment, compositions (A), (B) and (C), more specifically composition (A) then (B) then (C) or (B) then (A) then (C), are applied to wet or dry keratin fibres, successively and without intermediate rinsing.

In accordance with a second variant of this second embodiment, the composition resulting from mixing prior to application of compositions (A) and (B) then oxidizing composition (C) are applied to keratin fibres, successively and without intermediate rinsing.

According to a third variant of this embodiment, a composition obtained by extemporaneous mixing, before application, of compositions (A), (B) and (C) is applied to the wet or dry keratin fibres. This variant is preferred. According to this variant, the final composition resulting from the mixture of (A), (B) and (C) contains at least 20% by weight of fatty substance. In this variant, the weight ratios R1 of the amounts of compositions (A)+(B)/(C) and R2 of the amounts of compositions (A)/(B) vary from 0.1 to 10 and preferably from 0.3 to 3.

Preferably, compositions (A), (B) and (C) are mixed before use.

Both for colouring and lightening, the mixtures obtained are then applied to the keratin fibres with a leave-on time of about 3 to 50 minutes, preferably about 5 to 35 minutes; the keratin fibres are rinsed, washed with shampoo, rinsed again then dried.

More particularly, the chemical oxidizing agent(s) are chosen from hydrogen peroxide, urea hydrogen peroxide, alkali metal bromates or ferricyanides, peroxygenated salts, for instance alkali metal or alkaline-earth metal persulfates, perborates and percarbonates, and also peracids and their precursors. One or more redox enzymes such as laccases, peroxidases and 2-electron oxidoreductases (such as uricase), optionally in the presence of their respective donor or cofactor, may also be used as oxidizing agent. Preferably, the oxidizing agent or agents are chosen from hydrogen peroxide, urea hydrogen peroxide or alkali metal bromates or ferricyanides.

This chemical oxidizing agent is advantageously formed from hydrogen peroxide especially in aqueous solution (aqueous hydrogen peroxide solution), whose concentration may range more particularly from 0.1% to 50% by weight, more preferably still from 0.5% to 20% by weight and better still from 1% to 15% by weight relative to the weight of the oxidizing composition.

With the goal of lightening and depending on the desired degree of lightening, the hydrogen peroxide can be combined with one or more peroxygenated salts.

The oxidizing composition is in various forms, for instance a solution, an emulsion or a gel.

Compositions (B) and (C) may optionally comprise one or more conventional solvents and additives, such as those indicated previously.

In addition, independently of the embodiment used, the mixture present on the fibres (resulting either from the extemporaneous mixing of the compositions, or from the successive application of these compositions) is left in place for a time, generally from about 1 minute to 1 hour and preferably from 5 minutes to 35 minutes.

The temperature during the method is conventionally between room temperature (between 15 and 25° C.) and 80° C. and preferably between room temperature and 60° C.

After the treatment, the human keratin fibres are optionally rinsed with water, optionally washed with a shampoo and then rinsed with water, before being dried or left to dry.

The present invention also relates to a first multi-compartment device using a first compartment containing the aqueous cosmetic composition (A) as defined hereinbefore, a second compartment containing a cosmetic composition (C) comprising one or more chemical oxidizing agents, and one or more oxidative dyes, and optionally one or more alkaline agents being used in the aqueous cosmetic composition according to the invention (A), or in a distinct dyeing composition (B) contained in a third compartment.

Specifically, the device comprises a first compartment containing the aqueous cosmetic composition (A) as defined hereinbefore, a second compartment containing the dyeing composition (B) comprising one or more oxidative dyes, and optionally one or more alkaline agents, and a third compartment containing an oxidizing composition (C).

The present invention also relates to a second multi-compartment device using a first compartment containing the aqueous cosmetic composition (A) as defined hereinbefore and optionally comprising one or more alkaline agents, a second compartment containing a cosmetic composition (C) comprising one or more chemical oxidizing agents.

The examples that follow serve to illustrate the invention without, however, being limiting in nature.

EXAMPLES

Example 1

The following compositions are prepared (quantities expressed in grams)

| Name | A1 (Invention) |
|---|---|
| Oxyethylenated lauryl alcohol (2EO) | 10.85 |
| Unprotected alkyl ($C_8/C_{16}$) polyglucoside (1,4) in aqueous solution at 53% (pH 11.5 to 12.5) Cocoglucoside | 10.85 |
| Fumed silica of hydrophobic nature Silica dimethyl silylate | 11.1 |
| Demineralized water | 10 |
| Liquid petrolatum | 57.2 |

Cosmetic Composition B:

| | 100 g |
|---|---|
| 1-Methyl-2,5-diaminobenzene | 2.53 |
| 1,3-Dihydroxybenzene (resorcinol) | 2.2 |
| 6-Hydroxybenzomorpholine | 0.11 |
| 1-Hydroxy-3-amino-benzene | 0.4 |
| 1-β-Hydroxyethyloxy-2,4-diaminobenzene dihydrochloride | 0.066 |
| Monoethanolamine | 15.1 |
| Hydroxyethyl cellulose | 1.5 |
| Powdered sodium metabisulfite | 0.7 |
| Ascorbic acid | 0.25 |
| Diethylenetriaminepentaacetic acid | 1 |
| Propylene glycol | 6.2 |
| Ethanol | 8.25 |
| Hexylene glycol | 3 |
| Dipropylene glycol | 3 |
| Demineralized water | qsp 100% |

Composition (C1)

| Fatty alcohols | 2.28 |
|---|---|
| non-ionic surfactants | 1.42 |
| Glycerol | 0.5 |
| Hydrogen peroxide | 6 |
| Hydrogen peroxide stabilizers | 0.12 |
| Demineralized water | qsp 100 |

At the time of use, first the following are mixed:

9 grams of the aqueous composition (A1), 1 gram of composition (B)

10 grams of the oxidizing aqueous composition (C1).

The mixture obtained, whose pH is about 10 (±0.1), is then applied to tresses of virgin Caucasian hair with 90% natural white hairs (NW), the "mixture/tress" bath ratio is 10/1 (g/g) respectively, the leave-on time is 30 minutes at 27° C.

After this leave-on time, the tresses are washed with iNOA POST shampoo, rinsed then dried in a hood dryer at 60° C.

The colour of the tresses was evaluated in the CIE L*a*b* system, using a Minolta Spectrophotometer CM2600D colorimeter, In this system L*a*b*, the three parameters designate the colour intensity (L*), a* indicates the green/red colour axis and b* the blue/yellow colour axis respectively.

The variation in colour between the tresses of white hair comprising 90% natural white hairs (90 NW) untreated (control) and after treatment or dyeing are defined by (ΔE*) according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured on tresses of hair after dyeing and $L_o^*$, $a_o^*$ and $b_o^*$ represent the values measured on tresses of non-coloured virgin hair. The greater the value of ΔE*, the better the colour coverage.

Results

The results are collated in the following table:

| | L* | a* | b* | ΔE* |
|---|---|---|---|---|
| Untreated hair (NW) | 57.04 | 0.91 | 12.47 | — |
| Compositions (A1) + (B) + (C1) (Invention) | 18.95 | 2.42 | 3.57 | 39.14 |

A powerful colour is obtained and observed on the tress of hair when composition (A1) is used.

Example 2

The following compositions are prepared (quantities expressed in grams):

| Ingredients | Composition A2 (Invention) |
|---|---|
| Oxyethylenated lauryl alcohol (2EO) | 2 |
| Unprotected alkyl ($C_8/C_{10}/C_{12}/C_{14}$ 34/24/29/10)polyglucoside (1,4) in aqueous solution at 53% DECYL GLUCOSIDE | 1.96 |
| Demineralized water | 15 |

-continued

| Ingredients | Composition A2 (Invention) |
|---|---|
| SMDI/polyethylene glycol polymer with decyl chain endings in hydroxglycolic solution PEG-150/DECYL ALCOHOL/SMDI COPOLYMER (Aculyn 44) | 0.5 |
| Kaolinite | 2.04 |
| Liquid petrolatum | qsp 100 |

Composition (C2):

| | |
|---|---|
| Liquid petrolatum | 20 |
| Fatty alcohols | 2.28 |
| non-ionic surfactants | 1.42 |
| Glycerol | 0.5 |
| Hydrogen peroxide | 6 |
| Hydrogen peroxide stabilizers | 0.12 |
| Demineralized water | qsp 100 |

At the time of use, the following are mixed:
10 grams of the aqueous composition (A2),
4 grams of composition (B)
15 grams of the oxidizing aqueous composition (C2).

The mixture obtained, whose pH is about 9.8 (±0.1), is then applied to a tress of virgin Caucasian hair with 90% natural white hairs (NW). The "mixture/tress" bath ratio is from 10/1 (g/g) respectively, the leave-on time is 30 minutes at 27° C.

After this leave-on time, the tress is washed with iNOA POST shampoo, rinsed then dried in a hood dryer at 60° C.
Results
The results are collated in the following table:

| | L* | a* | b* | ΔE* |
|---|---|---|---|---|
| Untreated hair (NW) | 58.97 | 0.58 | 15.22 | — |
| Hair coloured with the compositions (A2) + (B) + (C2) (Invention) | 18.1 | 1.63 | 2.33 | 42.87 |

Using composition (A2) according to the invention in an oxidative colouring method, a powerful colour is obtained on the hair tress.

The invention claimed is:
1. Aqueous cosmetic composition comprising:
(i) one or more fatty substances in a content ranging from 40% to 80% by weight, relative to the total weight of the cosmetic composition,
(ii) one or more oxyethylenated fatty alcohols having a number of oxyethylenes less than or equal to 10,
(iii) one or more alkylpolyglucoside-type non-ionic surfactants, and
(iv) one or more thickening agents, wherein the one or more thickening agent are associative polymers.
2. Cosmetic composition according to claim 1, characterized in that the fatty substance(s) are chosen from compounds that are liquid or pasty at room temperature and atmospheric pressure.
3. Cosmetic composition according to claim 1, characterized in that the fatty substance(s) are chosen from $C_6$-$C_{16}$ lower alkanes, non-silicone oils of animal, plant, mineral or synthetic origin, non-oxyalkylenated fatty alcohols, fatty acid and/or fatty alcohol esters, non-silicone waxes and silicones.
4. Cosmetic composition according to claim 1, characterized in that the fatty substance(s) are chosen from liquid petrolatum, 2-octyldodecanol, perhydrosqualene, polydecenes, liquid esters of fatty acids and/or of fatty alcohols, or their mixtures.
5. Cosmetic composition according to claim 1, characterized in that the oxyethylenated fatty alcohols have the following structure:

in which:
R denotes a saturated or unsaturated, linear or branched radical containing from 6 to 40 carbon atoms and Z denotes an oxyethylenated radical having the following formula (I):

$$-CH_2-CH_2-O- \qquad (I)$$

m denotes the number of ethylene oxide groups below 10.
6. Cosmetic composition according to claim 1, characterized in that the oxyethylenated fatty alcohols are saturated or unsaturated, linear fatty alcohols, containing from 10 to 20 carbon atoms and from 2 to 8 ethylene oxide groups.
7. Cosmetic composition according to claim 1, characterized in that the alkylpolyglucoside-type non-ionic surfactants are represented by the following general formula (II):

in which $R_1$ designates a linear or branched alkyl and/or alkenyl radical comprising from about 8 to 24 carbon atoms, an alkylphenyl radical in which the linear or branched alkyl group comprises from about 8 to 24 carbon atoms, $R_2$ denotes an alkylene radical comprising from 2 to 4 carbon atoms, L designates a reducing sugar containing from 5 to 6 carbon atoms, a designates a value ranging from 0 to 10, and b designates a value ranging from 1 to 15.
8. Cosmetic composition according to claim 7, characterized in that the alkylpolyglucoside-type non-ionic surfactants are compounds having formula (II) in which $R_1$ designates a linear or branched alkyl and/or alkenyl radical containing from 9 to 14 carbon atoms, a designates a value ranging from 0 to 3 L designates glucose, fructose or galactose and the degree of polymerization (S) of the saccharide, i.e. the value of b in the formula (II), may range from 1 to 15.
9. Cosmetic composition according to claim 1, characterized in that it comprises water in a content ranging from 5% to 30% by weight, relative to the total weight of the composition.
10. Cosmetic composition according to claim 1, characterized in that it comprises one or more alkaline agents.
11. Cosmetic composition according to claim 1, characterized in that it comprises one or more oxidative dyes.
12. Method for bleaching keratin fibres, particularly human keratin fibres, comprising the application to said fibres of a cosmetic composition as defined according to claim 1, in the presence of a composition comprising one or more chemical oxidizing agents, for long enough to develop the desired colour.

13. Method for colouring keratin fibres, particularly human keratin fibres, comprising the application to said fibres of a cosmetic composition as defined according to claim 11, in the presence of a composition comprising one or more chemical oxidizing agents, for long enough to develop the desired colour.

14. Multi-compartment device using a first compartment containing the aqueous cosmetic composition as defined according to claim 1, a second compartment containing a cosmetic composition comprising one or more oxidizing agents, and one or more oxidative dyes, and optionally one or more alkaline agents being used in said aqueous cosmetic composition, or in a distinct composition contained in a third compartment.

15. Second multi-compartment device using a first compartment containing the aqueous cosmetic composition (A) as defined according to claim 1 and comprising one or more alkaline agents, a second compartment containing a cosmetic composition (C) comprising one or more chemical oxidizing agents.

16. A method according to claim 12, characterized in that the chemical oxidizing agent is hydrogen peroxide.

17. A multi-compartment device according to claim 14, characterized in that the oxidizing agent is hydrogen peroxide.

18. A multi-compartment device according to claim 15, characterized in that the chemical oxidizing agent is hydrogen peroxide.

19. Aqueous cosmetic composition comprising:
(i) one or more fatty substances in a content ranging from 40% to 80% by weight, relative to the total weight of the cosmetic composition,
(ii) one or more oxyethylenated fatty alcohols having a number of oxyethylenes less than or equal to 10,
(iii) one or more alkylpolyglucoside-type non-ionic surfactants, and
(iv) one or more thickening agents chosen from non-ionic, anionic, cationic or amphoteric associative polymers.

* * * * *